US006627646B2

(12) United States Patent
Bakale et al.

(10) Patent No.: US 6,627,646 B2
(45) Date of Patent: Sep. 30, 2003

(54) NORASTEMIZOLE POLYMORPHS

(75) Inventors: Roger P. Bakale, Shrewsbury, MA (US); Chris Senanayake, Shrewsbury, MA (US); Yaping Hong, Princeton, NJ (US); Kostas Saranteas, Peabody, MA (US); Martin P. Redmon, Oxford, MA (US); Stephen A. Wald, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/907,556

(22) Filed: Jul. 17, 2001

(65) Prior Publication Data

US 2003/0100581 A1 May 29, 2003

(51) Int. Cl.⁷ ..................... A61K 31/445; C07D 401/12

(52) U.S. Cl. ................ 514/322; 514/303; 514/313; 546/199

(58) Field of Search ................ 514/303, 313, 514/322; 546/199

(56) References Cited

U.S. PATENT DOCUMENTS

| | | | |
|---|---|---|---|
| 4,695,569 A | 9/1987 | Janssens et al. | 514/258 |
| 4,835,161 A * | 5/1989 | Janssens et al. | 514/303 |
| 5,817,823 A | 10/1998 | Hong et al. | 546/199 |
| 5,922,737 A | 7/1999 | Maynard et al. | 514/318 |
| 6,124,320 A | 9/2000 | Woosley et al. | 514/322 |

OTHER PUBLICATIONS

U.S. Pharmacopia #23 "national Formulary #18" (1995) p. 1843–1844, X-ray diffraction.*
Janssens et al. "New Antihistaminic N–Heterocyclic 4–Piperidinamines. 2. Synthesis and Antihistaminic Activity of . . . " *J. Med. Chem. 28*, 1934–1943 (1984).
Hong et al. "Palladium Catalyzed Amination of 2–Chloro–1, 3–Azole Derivatives: Mild Entry to Potent . . . " *Tetrahedron Letters 38*, 5607–5610 (1997).

* cited by examiner

*Primary Examiner*—Ceila Chang
(74) *Attorney, Agent, or Firm*—Heslin Rothenberg Farley & Mesiti P.C.

(57) ABSTRACT

Polymorphic crystalline forms of the antihistaminic drug norasternizole are disclosed. Processes for the production of the preferred polymorph are also disclosed.

13 Claims, 9 Drawing Sheets

NORASTEMIZOLE POLYMORPHS

FIELD OF THE INVENTION

The invention relates to polymorphic crystalline forms of the antihistaminic drug norastemizole and to processes for the production of the preferred polymorph.

BACKGROUND OF THE INVENTION

Norastemizole, 1-[(4-fluorophenyl)methyl]-N-4-piperidinyl-1H-benzimidazol-2-amine, is an active metabolite of the histamine $H_1$-receptor antagonist astemizole (HISMANAL™). It is described in U.S. Pat. No. 6,124,320 for use in the treatment of allergic disorders.

The polymorphic behavior of drugs can be of crucial importance in pharmacy and pharmacology. Polymorphs are, by definition, crystals of the same molecule having different physical properties as a result of the order of the molecules in the crystal lattice. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing: for example, one polymorph might be more likely to form solvates or might be difficult to filter and wash free of impurities (i.e particle shape and size distribution might be different between one polymorph relative to the other).

Each pharmaceutical compound has an optimal therapeutic blood concentration and a lethal concentration. The bio-availability of the compound determines the dosage strength in the drug formulation necessary to obtain the ideal blood level. If the drug can crystallize as two or more polymorphs differing in bio-availability, the optimal dose will depend on the polymorph present in the formulation. Some drugs show a narrow margin between therapeutic and lethal concentrations. Chloramphenicol-3-palmitate (CAPP), for example, is a broad spectrum antibiotic known to crystallize in at least three polymorphic forms and one amorphous form. The most stable form, A, is marketed. The difference in bio-activity between this polymorph and another form B, is a factor of eight—creating the possibility of fatal overdosages of the compound if unwittingly administered as form B due to alterations during processing and/or storage. Therefore, regulatory agencies, such as the US Food and Drug Administration, have begun to place tight controls on the polymorphic content of the active component in solid dosage forms. In general, for drugs that exist in polymorphic forms, if anything other than the pure thermodynamically preferred polymorph is to be marketed, the regulatory agency will require batch-by-batch monitoring. Thus, it becomes important for both medical and commercial reasons to produce and market the most thermodynamically stable polymorph, substantially free of other kinetically favored polymorphs.

From thermodynamic considerations, only one polymorph will be stable; the one with the lowest free energy at a given temperature and pressure. From the industrial crystallization point of view, however, thermodynamic stability is not sufficient to ensure that the stable polymorph will always be produced. During primary nucleation, in the absence of seed crystals, it is the unstable polymorph or pseudo polymorph in the form of a hydrate or solvate that tends to crystallize first (kinetic form). This is, in essence, Ostwald's Rule of Stages, which posits that an unstable system does not transform directly to the most stable state. Instead, it transforms to a transient state accompanied by the smallest loss of free energy. The eventual transition(s) to the most stable phase is inevitable but the transformation can be extremely fast or extremely slow depending on the process conditions present. Most transformations occur in suspension and are solvent mediated. Some polymorphic transformations can be reversible when the relative solubilities of the polymorphs invert over a range of temperatures (enantiotropic). Other transformations are irreversible (monotropic) over a broad range of temperatures.

Although several syntheses of norastemizole are described in the literature, polymorphism of the solid product is not disclosed. Applicants have now discovered that solid norastemizole exists in two polymorphic forms. As is shown in the results of applicants' experiments below, the product produced by methods previously described in the literature of which applicants are aware is in every case composed of greater than 80% of the kinetically favored polymorph and less than 20% of the desired thermodynamically stable polymorph. Those references which have been examined include:(1) Janssen et al. U.S. Pat. No. 4,695,569, column 24, lines 22–32;(2) Hong et. al. U.S. Pat. No. 5,817,823, column 32, lines 9–18; column 33, lines 16–23; column 36, lines 31–41; and column 43, lines 19–24; and (3) Maynard et al. U.S. Pat. No. 5,922,737, and column 39, lines 20–30.

SUMMARY OF THE INVENTION

In one aspect, the invention relates to norastemizole in the form of a crystalline solid comprising at least 95% of a first polymorph (hereinafter referred to as polymorph A) defined by the X-ray powder diffraction pattern (including both characteristic peaks and intensities) shown below.

TABLE 1

| No. | 2θ, degrees | d |
|---|---|---|
| 1 | 9.0329 | 6.78217 |
| 2 | 10.24 | 8.63159 |
| 3 | 10.588 | 8.34866 |
| 4 | 11.7273 | 7.54003 |
| 5 | 12.5417 | 7.05218 |
| 6 | 13.38 | 6.61217 |
| 7 | 13.6284 | 6.4922 |
| 8 | 14.5846 | 6.06864 |
| 9 | 15.8358 | 5.59185 |
| 10 | 17.26 | 5.13352 |
| 11 | 18.1 | 4.89713 |
| 12 | 19.32 | 4.59055 |
| 13 | 19.62 | 4.52103 |
| 14 | 20.12 | 4.40979 |
| 15 | 20.5005 | 4.3288 |
| 16 | 20.9946 | 4.22802 |
| 17 | 21.22 | 4.18362 |
| 18 | 21.8351 | 4.06714 |
| 19 | 22.0887 | 4.02101 |
| 20 | 22.9427 | 3.87323 |
| 21 | 23.56 | 3.77313 |
| 22 | 24.7 | 3.6015 |
| 23 | 25.4419 | 3.49814 |
| 24 | 26.98 | 3.3021 |
| 25 | 27.5 | 3.24083 |
| 26 | 27.98 | 3.18632 |
| 27 | 29 | 3.07652 |
| 28 | 29.46 | 3.02952 |
| 29 | 29.8 | 2.99573 |
| 30 | 30.66 | 2.91363 |
| 31 | 31.0238 | 2.88029 |
| 32 | 31.991 | 2.79538 |
| 33 | 32.8 | 2.72826 |

This is the more thermodynamically stable polymorph. The kinetically favored polymorph B exhibits an XRPD pattern as follows:

TABLE 2

| No. | 2θ, degrees | d |
|---|---|---|
| 1 | 9.0453 | 9.76879 |
| 2 | 10.4129 | 8.48865 |
| 3 | 11.5309 | 7.66801 |
| 4 | 13.0056 | 6.80166 |
| 5 | 13.42 | 6.59255 |
| 6 | 15.54 | 5.69762 |
| 7 | 15.9321 | 5.55827 |
| 8 | 16.26 | 5.44691 |
| 9 | 17.3399 | 5.11004 |
| 10 | 18.1381 | 4.88693 |
| 11 | 19.54 | 4.53936 |
| 12 | 20.125 | 4.40871 |
| 13 | 20.56 | 4.3164 |
| 14 | 21.22 | 4.18362 |
| 15 | 23.08 | 3.8505 |
| 16 | 23.78 | 3.73871 |
| 17 | 24.3 | 3.65987 |
| 18 | 25.0012 | 3.55879 |
| 19 | 26.34 | 3.38087 |
| 20 | 27.1506 | 3.28174 |
| 21 | 27.92 | 3.19303 |
| 22 | 28.76 | 3.10165 |
| 23 | 29.32 | 3.04367 |
| 24 | 29.76 | 2.99966 |
| 25 | 30.14 | 2.9627 |
| 26 | 31.42 | 2.84487 |
| 27 | 32.16 | 2.78107 |
| 28 | 32.56 | 2.74782 |

In another aspect, the invention relates to a process for producing crystalline norastemizole, predominantly as polymorph A. In a generic sense the process comprises:

(a) dissolving norastemizole in just enough solvent to achieve dissolution at a first elevated temperature;

(b) adding an amount of anti-solvent just sufficient to initiate crystallization at the first temperature (sufficient means that less than 5% of the norastemizole crystallizes);

(c) stirring the first temperature for a period of time to allow crystallization of a small amount (less than 5%) of the norastemizole; the combination of time and low equilibration of the crystallizing norastemizole to temperature is such as to allow equilibration of the crystallizing norastemizole to greater than 95% polymorph A;

(d) adding a second portion of anti-solvent at the same elevated first temperature and over a second period of time such that norastemizole that crystallizes during the second addition of anti-solvent is greater than 95% of the polymorph of claim 1; to accomplish this, the second portion of anti-solvent is of sufficient amount to produce ultimate crystallization of at least 85% of the norastemizole at a lower temperature, but the amount and rate of addition are kept such that the solubility curve for polymorph B at the temperature of addition is not crossed; and (e) stirring and cooling from the first, higher temperature to a second, lower temperature in a non-linear fashion over a third period of time such that no more than a 15% temperature drop occurs in the first half of the cooling time; in this fashion, at least 85% of the norastemizole is crystallized and greater than 95% of it is in the form of the polymorph A.

In a particular embodiment of the process aspect, the process comprises: (a) dissolving norastemizole in a solvent at a temperature between 70° C. and 110° C.; (b) adding an amount of anti-solvent sufficient to initiate crystallization at a temperature above 70° C.; (c) stirring at a temperature above 70° C. for at least one hour; (d) adding a second portion of anti-solvent at a temperature above 70° C. and over a period of at least 2 hours, in an amount sufficient to produce crystallization of at least 85% of dissolved norastemizole; and (e) stirring and cooling from above 70° C. to below 30° C. over the course of at least 6 hours in a non-linear fashion such that no more than a 15% temperature drop occurs in the first 3 hours.

In another aspect, the invention relates to norastemizole (predominantly in the form of polymorph A) produced by the process described above.

In another aspect, the invention relates to a method for treating allergic conditions in a mammal comprising administering a therapeutically effective amount of norastemizole in the form of polymorph A.

In another aspect, the invention relates to a pharmaceutical composition comprising a pharmaceutically acceptable carrier for a solid dosage form and norastemizole in the form of polymorph A.

DETAILED DESCRIPTION OF THE INVENTION

Applicants have investigated solid norastemizole using quantitative thermal analysis (OSC), x-ray powder diffraction (XRPD), and hot stage microscopy and have discovered two polymorphs of norastemizole. From these crystal structures, XRPD patterns were generated that match the patterns measured for products from the process described in the invention. Based on the data, the process of the invention, described below, produces a single polymorph (within the <5% limit of detection).

Figure 1:
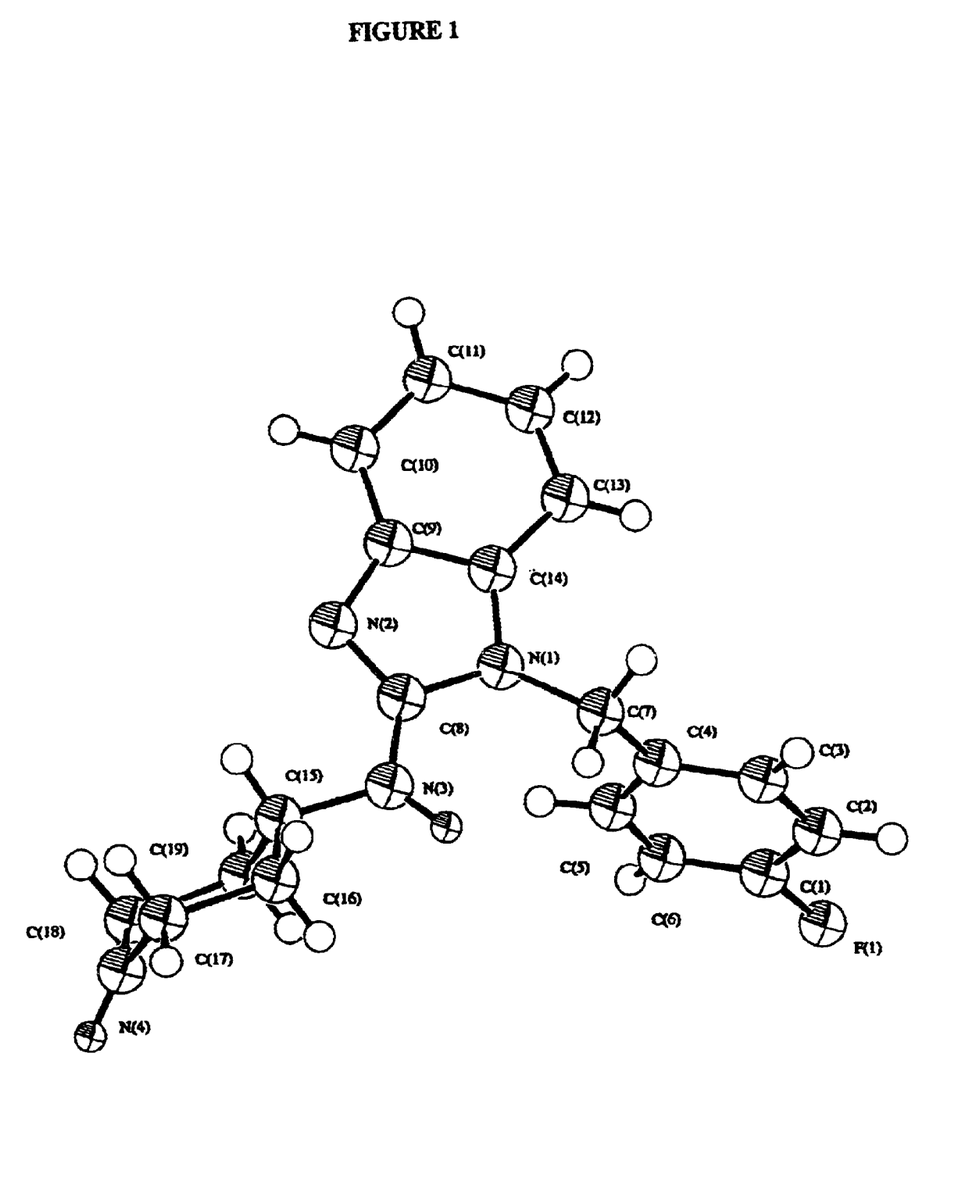
FIG. 1 is an Oak Ridge Thermal Ellipsoid Plot (ORTEP) drawing of the norastemizole molecule in one of the two conformations found in both polymorphs of crystalline norastemizole.
Figure 2:
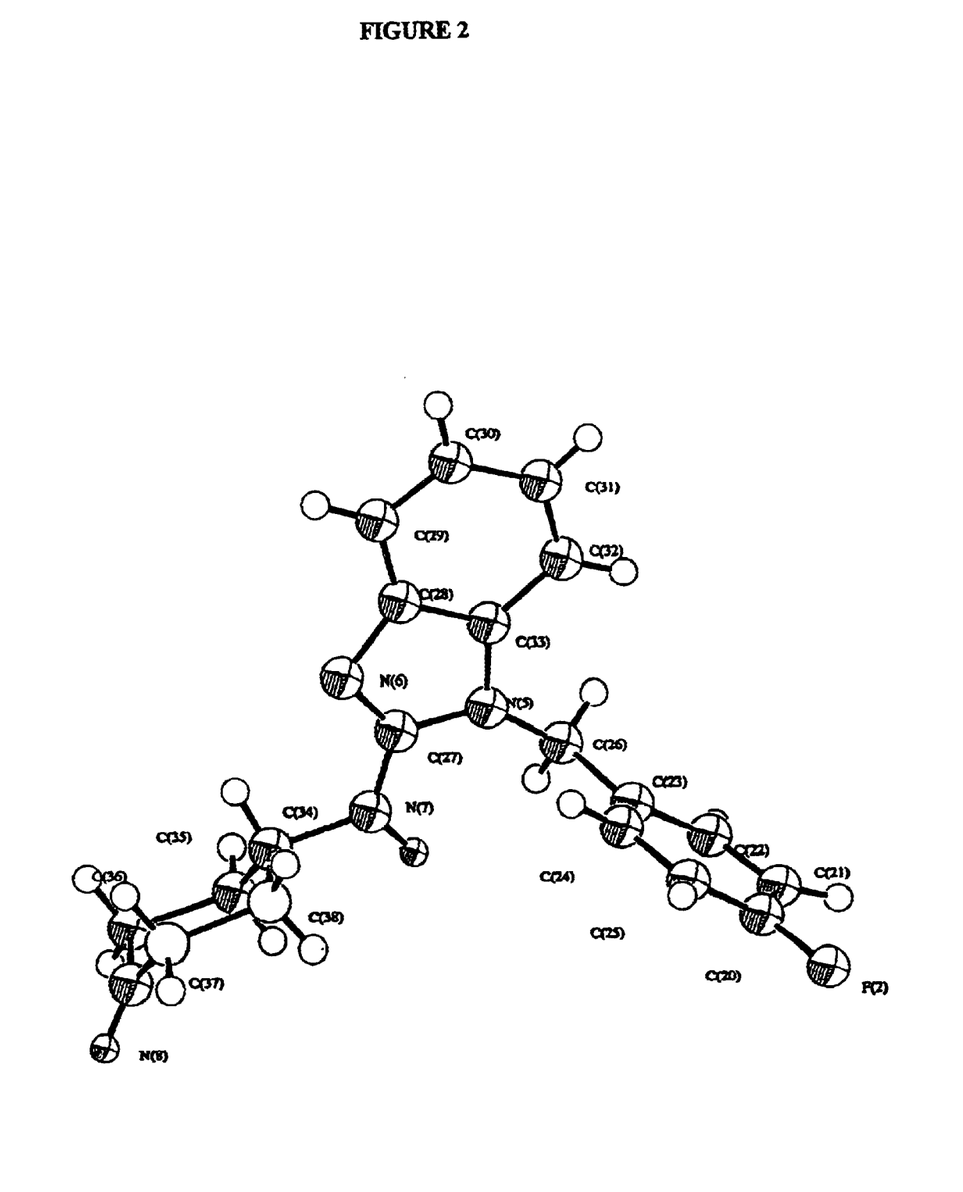
FIG. 2 is an ORTEP drawing of the norastemizole molecule in the other of the two conformations found in both polymorphs of crystalline norastemizole.

Both polymorph A and polymorph B have unit cells made up of two molecules and differ only in that a rotation of 180° has occurred around the N(1)-C(7) or N(5)-C(26) axis (FIG. 1 and FIG. 2). In polymorph A, the hydrogen bonding sequence is between molecules of the same type; in polymorph B, the hydrogen bonding sequence alternates. Therefore, the number of hydrogen bonds is the same; it is only the sequence that differs.

Figure 3:
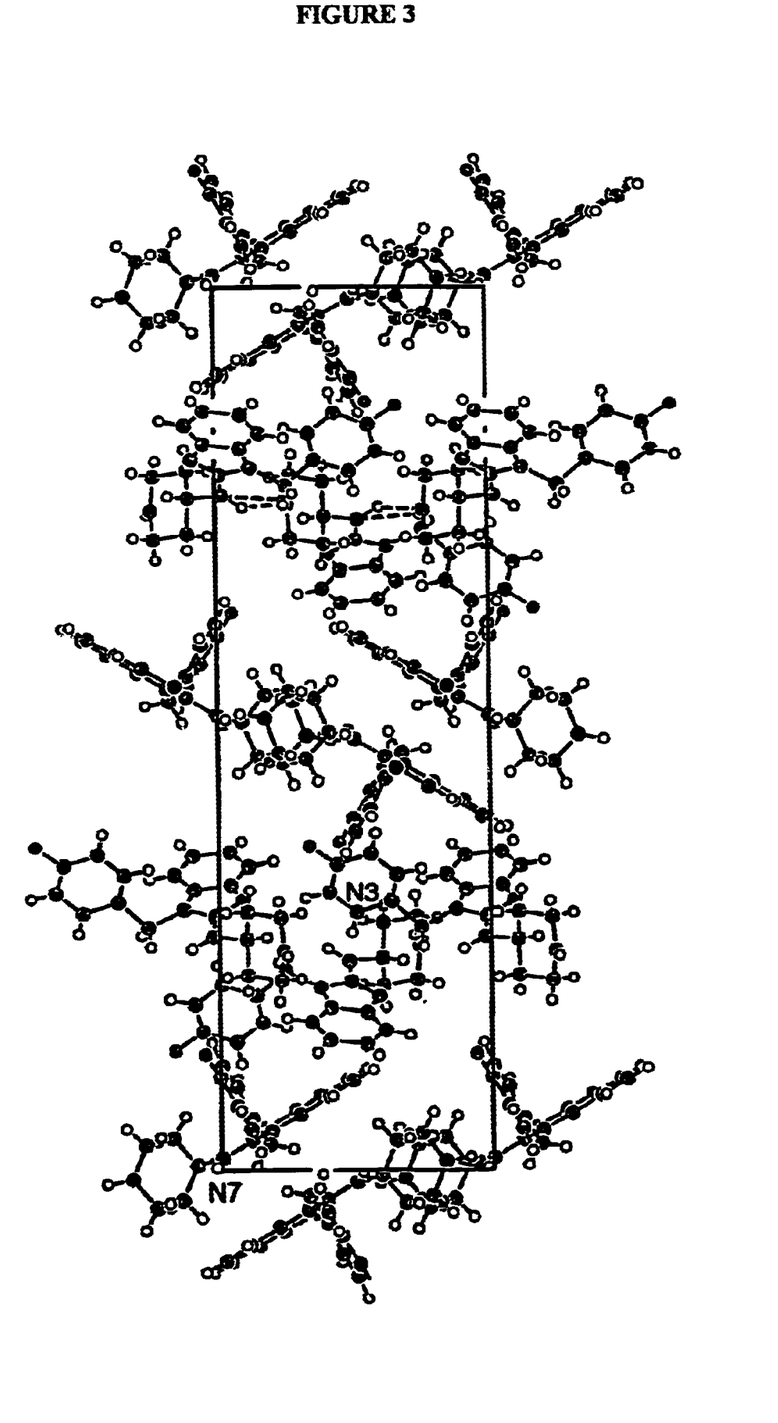
FIG. 3 is a representation of the arrangement of molecules of norastemizole in polymorph A of crystalline norastemizole.
Figure 4:
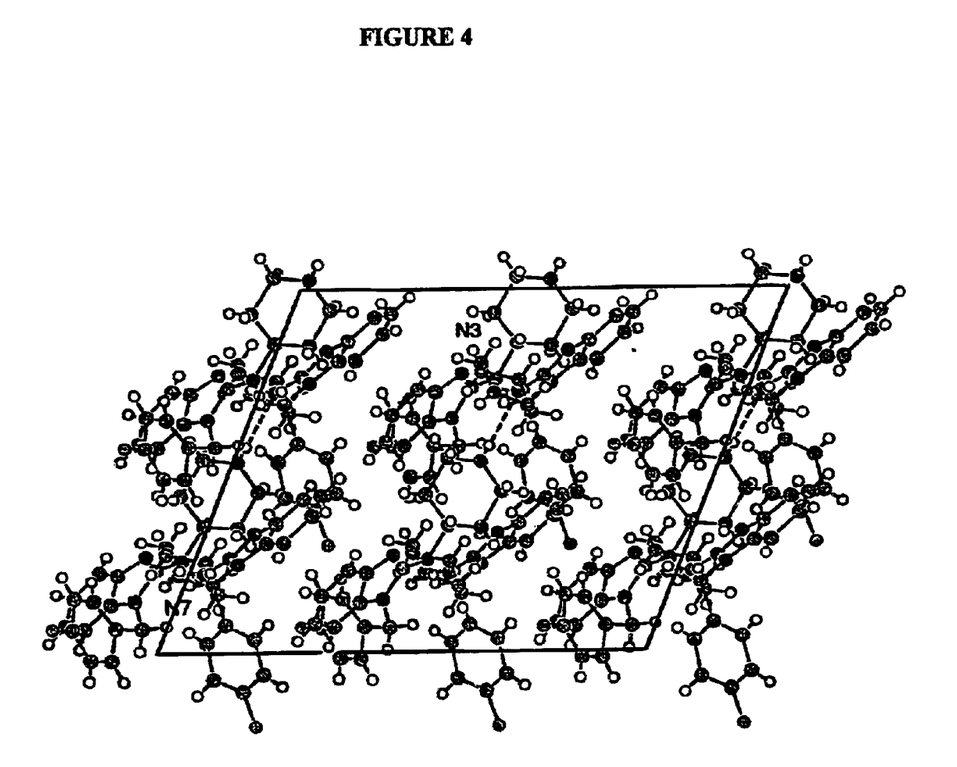
FIG. 4 is a representation of the arrangement of molecules of norastemizole in polymorph B of crystalline norastemizole.

The following is a brief description of the differences between the two polymorphs. Essentially each polymorph has two unique molecules—molecule type (1) (FIG. 1) and molecule type (2) (FIG. 2)—hydrogen bonded in a unit cell. In Polymorph A (FIG. 3), the hydrogen bonds are between molecules of type (1) or molecules of type (2) but not between the two types. In polymorph B (FIG. 4) molecules of type (1) and (2) are connected in an alternating fashion.

More specifically, the hydrogen bonding can be described in terms of the secondary amine groups in norastemizole. The respective nitrogen atoms can be described as the "linking" nitrogen and the "terminal" nitrogen. The linking nitrogen atoms are designated N(3) and N(7), the terminal nitrogen atoms are designated N(4) and N(8). Each molecule in a unit cell contains one linking nitrogen and one terminal nitrogen. By definition, molecule (1) contains N(3) and N(4) and molecule (2) contains N(7) and N(8).

In the polymorph A, the hydrogen bonding sequence in a cell is i.e., molecule 1 linking N . . . molecule 1 terminal N . . . molecule 1 linking N or i.e., molecule 2 linking N . . . molecule 2 terminal N . . . molecule 2 linking N . . . In other words, there is a sequence of linking-nitrogen to terminal-nitrogen hydrogen bonds between molecules either all of molecule (1) or all of molecule (2).

Polymorph B exhibits the following bonding sequence:

N(3)-H . . . N(8)-H . . . N(3) . . . and N(7)-H . . . N(4) . . . N(7)-H . . .

Molecule 1 linking N . . . molecule 2 terminal N . . . molecule 1 linking N, and molecule 2 linking N . . . molecule 1 terminal N . . . molecule 2 linking N. In this case there is still a linking-nitrogen hydrogen bonded to a terminal nitrogen, but the bonding is between a molecule type of (1) followed by a molecule of type (2).

Both space groups are non-centrosymmetric: $P2_12_12_1$ (Polymorph A) and Cc (Polymorph B). The formation of the crystal presumably depends on which of the two arrangements of hydrogen bonds occur in the initial crystal nuclei which form the seed for crystal growth. Polymorph B is kinetically favored.

| Parameter | Polymorph A | Polymorph B |
|---|---|---|
| Crystal Color/Habit | Colourless, plates | Colourless, blocks |
| Crystal system | Orthorhombic | Monoclinic |
| |  | |
| Lattice type | P | C-centered |
| Lattice parameters | a = 10.260(8)Å | a = 14.587(8)Å |
| | b = 33.335(3)Å | b = 14.111(5)Å |
| | c = 10.101(3)Å | c = 18.101(7)Å |
| | | β = 111.85(3)° |
| Volume | 3454(1)Å$^3$ | 3458(3)Å$^3$ |
| Space group | $P2_12_12_1$ (#19) | Cc (#9) |
| Z values (molecules/cell) | 8 | 8 |
| ρcalc | 1.247 g/cc | 1.246 g/cc |
| ρmeas | ND | 1.221 g/cc |

Figure 5:
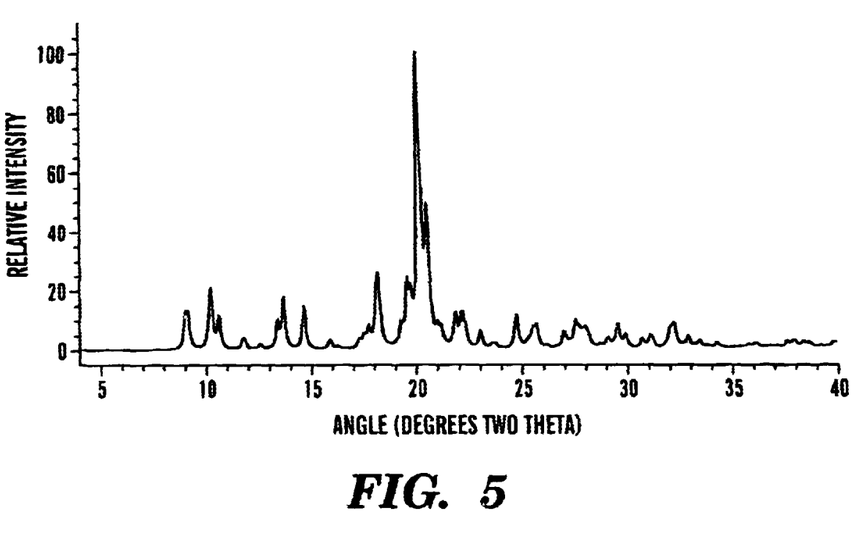
FIG. 5 is a calculated powder diffraction pattern for polymorph A of crystalline norastemizole.
Figure 6:
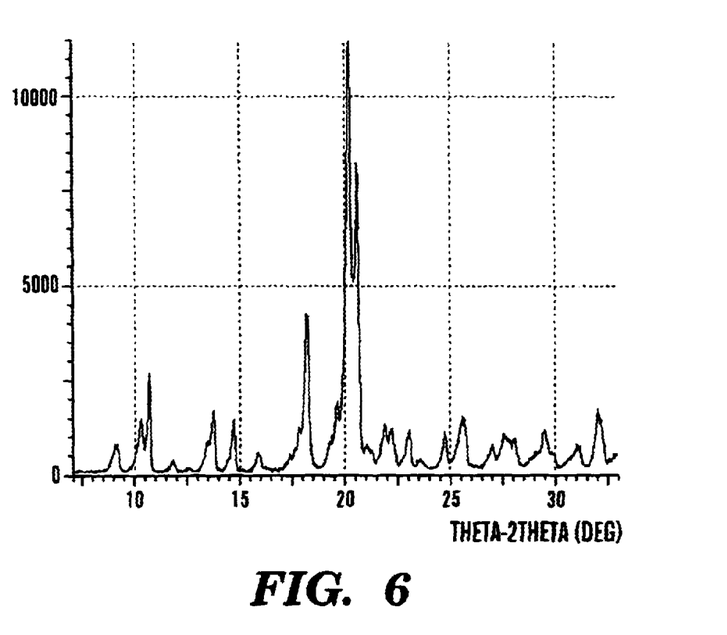
FIG. 6 is an experimentally obtained powder diffraction pattern for polymorph A of crystalline norastemizole.
Figure 7:
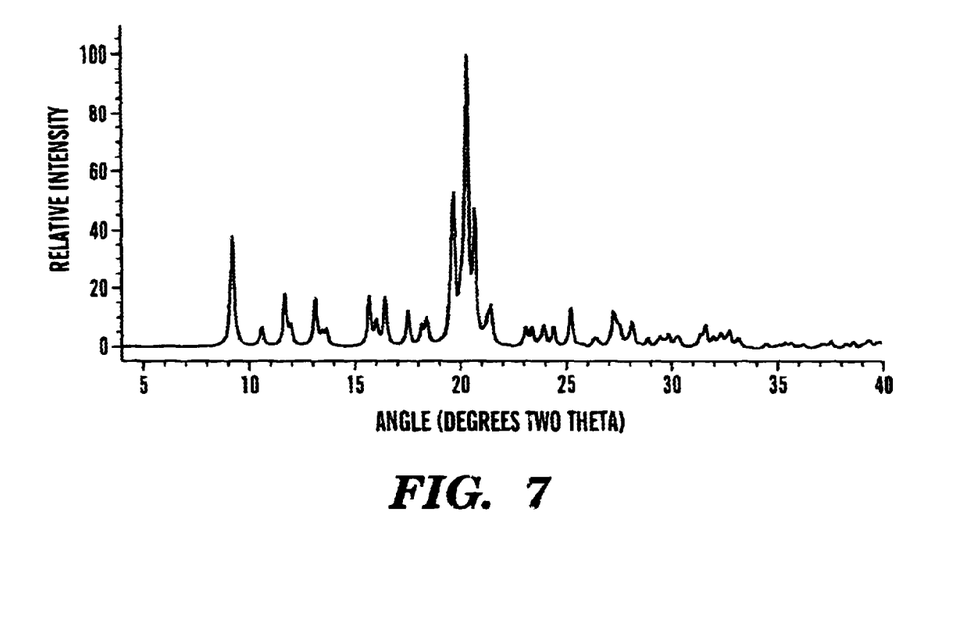
FIG. 7 is a calculated powder diffraction pattern for polymorph B of crystalline norastemizole.
Figure 8:
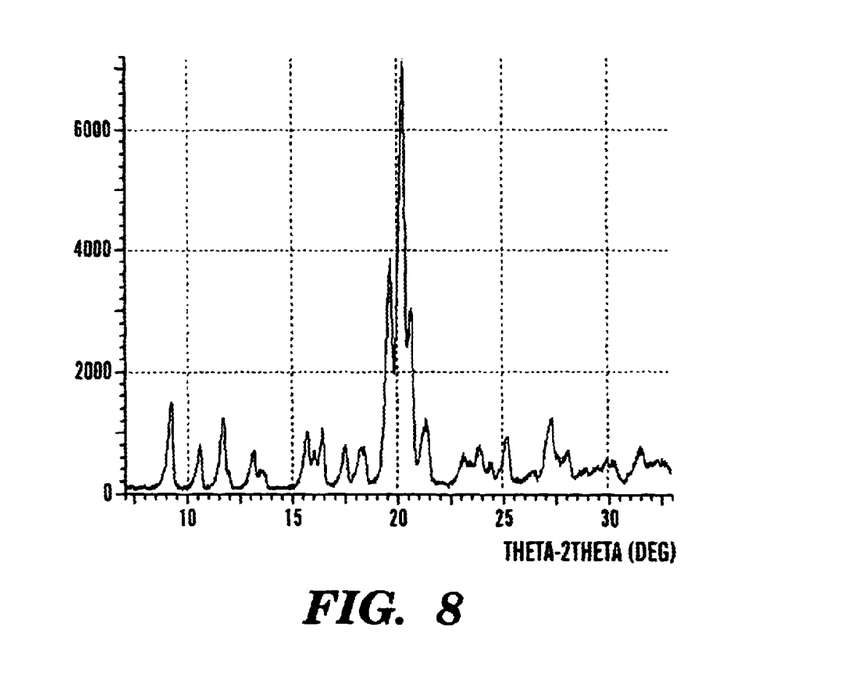
FIG. 8 is an experimentally obtained powder diffraction pattern for polymorph B of crystalline norastemizole.

A distinctive XRPD pattern is characteristic of each polymorph. FIGS. 5 and 6 show the XRPD patterns typical of polymorph A; FIGS. 7 and 8 show patterns typical of polymorph B. FIGS. 5 and 7 are calculated from the measured diffraction values for a single crystal. The X-ray intensities, which come from the diffraction of a well-formed single crystal, and the powder pattern, which would come from the same material if ground to a fine powder, are not exactly equivalent. In particular, the single crystal experiment aligns each crystal reflecting plane exactly in the reflecting position, while the powder pattern is derived from many planes, most of them slightly misaligned with respect to the perfect reflecting angle. The magnitude of this difference depends (among other things) on the diffracting angle. However, the relationship between the single crystal measurement and the corresponding powder pattern is well known and can be calculated. FIGS. 6 and 8 are patterns measured directly from powders of the respective polymorphs. The unique reflections are shown in Table 3 below. Reflections are considered "unique" if no reflection is observed within ±0.2° when comparing 2θ values for the two norastemizole forms.

TABLE 3

Unique Reflections for Norastemizole Forms A and B

| Form A (2θ) | Form B (2θ) |
|---|---|
| 11.7273 | 11.5309 |
| 12.5417 | 13.0056 |
| 13.6284 | 15.54 |
| 14.5846 | 16.26 |
| 19.32 | 23.78 |
| 20.9946 | 24.3 |
| 21.8351 | 25.0012 |
| 22.0887 | 26.34 |
| 23.56 | 28.76 |
| 24.7 | 30.14 |
| 25.4419 | 31.42 |
| 27.5 | 32.56 |
| 29 | — |
| 30.66 | — |
| 31.0238 | — |
| 32.8 | — |

Early bulk drug lots of norastemizole prepared by applicants were found to be mixtures of the two polymorphs, A and B. The x-ray patterns of the two forms showed significant overlap. A Rietveld analysis was developed that allowed quantitative determination of Form B in Form A down to a detection limit at 5%. Upon analysis, it became apparent that the desired polymorph, in any reasonable degree of purity, could not be produced by the known procedures, and indeed, even a specific ratio of polymorphs was not consistently produced by the known procedures. As discussed above, such a situation is highly undesirable from both a medical and a regulatory standpoint. A comprehensive study was undertaken to identify critical process parameters that affect polymorph selectivity, to develop a fundamental model that explains all experimental observations, and to derive a crystallization process that reproducibly provides norastemizole in which greater than 95% of the total solid is in the form of the desired polymorph, Form A.

Figure 9:
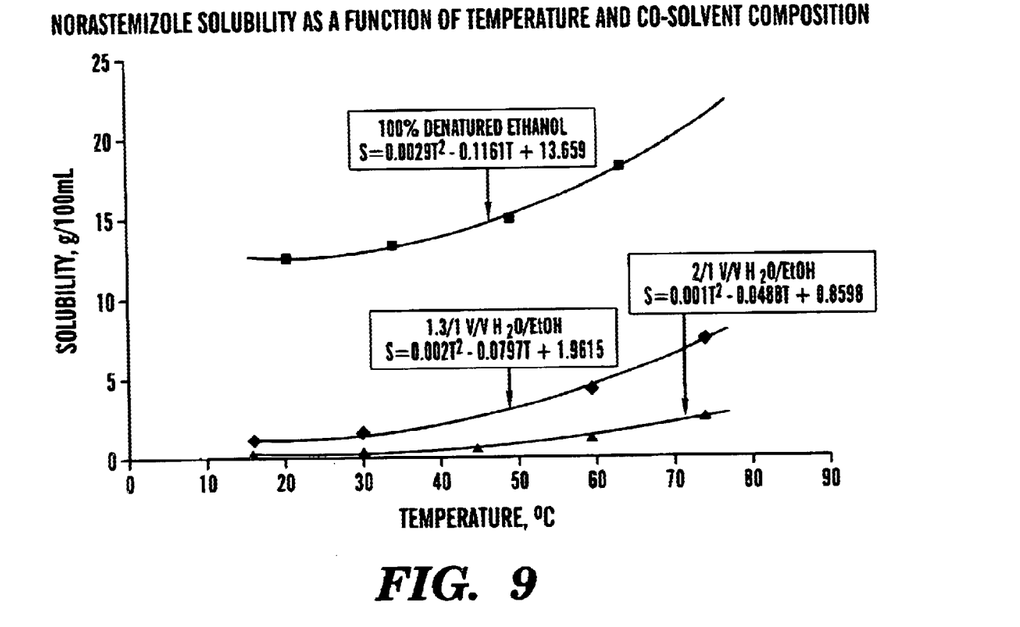
FIG. 9 is a graph of the solubility of norastemizole polymorph A as a function of temperature in three different solvent systems.
Figure 10:
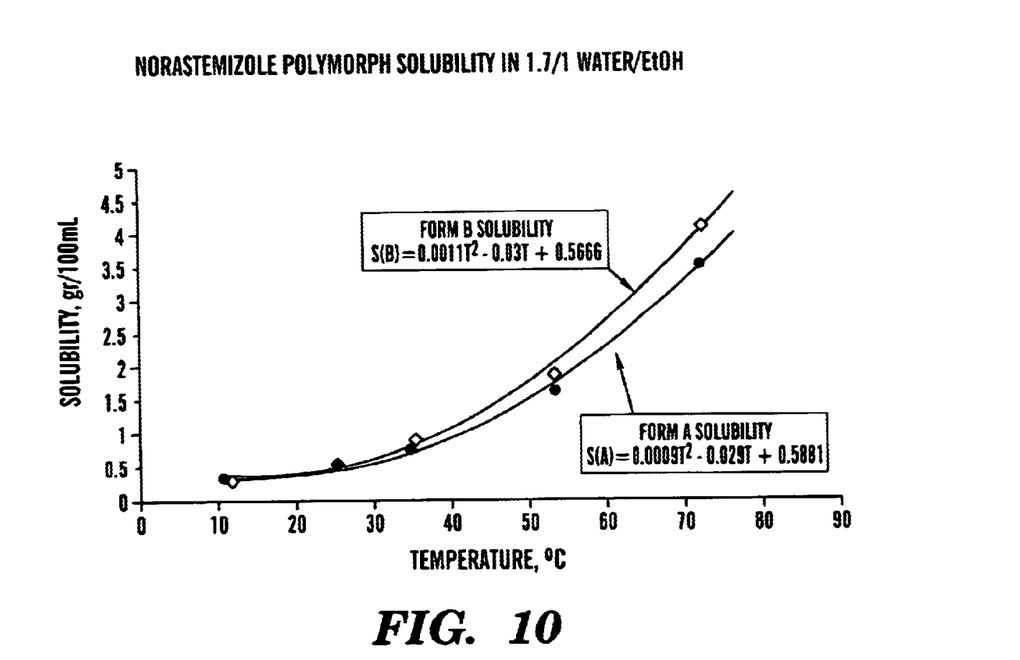
FIG. 10 is a graph of the solubilities of norastemizole polymorph A and polymorph B as a function of temperature in 17:10 water/ethanol.

The solubility of norastemizole in various ratios of co-solvent mixtures was determined in order to facilitate the recovery of material and to determine the level of supersaturation during crystallization. FIG. 9 illustrates the solubility of norastemizole Form A as a function of co-solvent composition and temperature for an ethanol and two water/ethanol co-solvent systems. In this description, and in the descriptions of all solvent mixtures herein, the ratios of solvents are given in volume-to-volume. FIG. 10 illustrates the solubility of the two polymorphs A and B as function of temperature in 17:10 water/ethanol. The results indicate that denatured ethanol with an anti-solvent addition (water) in excess of 13 to 10 by volume can give reasonable recovery yields, and that the solubility difference between Form A and Form B decreases as the temperature decreases with an enantiotropic transition temperature around 0–10° C.

The thermodynamic stability of the two enantiotropic solid forms of norastemizole was also studied by examining the isothermal stability of mixtures of the two polymorphs. Two different solvent systems were tested (17:10 water/ethanol and DMSO) at 6 different temperatures (5, 25, 40, 60, 80 and 100° C.). Samples were prepared by saturating the solvent system at the temperature of interest with pure form A, filtering, and, then, adding a 1:1 mixture of both seeds. The samples were then allowed to slurry for one week. Results summarized in Table 4 indicate that form A is the more thermodynamically stable form in the temperature region tested. Some residual B reported at high temperatures is most likely to cooling-induced crystallization during filtering. The high temperature sample is filtered using a filtration system that is at room temperature (i.e. causing an initial thermal shock and, as a result, generating some product precipitation in the kinetically favorable form B).

TABLE 4

Thermodynamic stability of Norastemizole Polymorphs as a function of Temperature

| Temperature, ° C. | Form B after one week slurry mixing in Ethanol/water | Form B after one week slurry mixing in DMSO |
|---|---|---|
| 5 | <5 | <5 |
| 25 | <5 | <5 |
| 40 | <5 | <5 |
| 60 | <5 | <5 |
| 80 | 12.0 | 10.7 |
| 100 | — | 13 |

The effect of temperature on the interconversion dynamic was measured by periodic sampling of a norastemizole slurry under the well-defined process conditions of controlled temperature and mixing in a 17:10 co-solvent ratio of water in denatured ethanol. Table 5 illustrates the effect of operating temperature on interconversion rate. As the temperature decreases, the interconversion rate decreases. An operating temperature of 70–76° C. leads to a complete interconversion within 4 hours.

TABLE 5

Effect of Temperature on Interconversion Dynamics

| Temperature | Time, hours | % Form B |
|---|---|---|
| 76° C. | 0 | 87 |
| 76° C. | 2 | 16 |
| 76° C. | 4 | <5 |
| 70° C. | 0.2 | 96 |
| 70° C. | 2.3 | 68 |
| 70° C. | 4.2 | <5 |
| 60° C. | 0.3 | 98 |
| 60° C. | 3.3 | 83 |
| 60° C. | 5.2 | 69 |
| 50° C. | 0.3 | 95 |
| 50° C. | 3.2 | 92 |
| 50° C. | 4.2 | 91 |

Table 6 below illustrates the effect of mixing energy on interconversion dynamics. As the agitation rate increases (improved mass transfer) the interconversion rate also increases. Operation at a low agitation rate requires a longer mixing time for complete interconversion, while a higher agitation leads to complete interconversion in less than 4 hours of operation at 76° C.

TABLE 6

Effect of Agitation Mixing Energy on Interconversion Dynamics (76° C.)

| Mixing Level | Agitation Rate | Time, hours | % Form B |
|---|---|---|---|
| Low | 435 RPM | 0 | 82 |
| Low | 435 RPM | 4 | 36 |
| High | 550 RPM | 0 | 87 |
| High | 550 RPM | 4 | <5 |

Table 7 below shows the effect of co-solvent composition on relative interconversion rates. While both co-solvent systems lead to good interconversion rates, a 2/1 co-solvent ratio leads to a faster interconversion (i.e. complete interconversion in under 3 hours) while maintaining other key factors constant (mixing energy and cooling profile).

TABLE 7

Effect of Co-solvent Composition on Inter-conversion Dynamics (76° C./550 RPM)

| Co-solvent System | Volumetric Ratio | Time, hours | % Form B |
|---|---|---|---|
| Water/denatured ethanol | 17:10 v/v | 0 | 87 |
| Water/denatured ethanol | 17:10 v/v | 3 | 14 |
| Water/denatured ethanol | 2:1 v/v | 0 | 88 |
| Water/denatured ethanol | 2:1 v/v | 3 | <5 |

As might be expected, as the relative amount of form A present increases, the inter-conversion rate also dramatically increases. A 50/50 mixture as the initial composition leads to a complete interconversion in less than 0.3 hours while a 3% form A initial composition shows a small interconversion (from 97% form B to 76% form B) in 2 hours. This effect is consistent with fundamental crystallization principles: as the relative concentration of the stable crystal increases, the available surface area for crystal growth also increases, and the rate of growth of the less soluble (form A) dramatically increases at the expense of the more soluble (form B). Interconversion to the thermodynamically more stable polymorph A results.

Four parameters that were initially considered possible result-effective variables in norastemizole morphology were the following: 1) amount of second water addition after seeding; 2) rate of second water addition; 3) agitation rate during second water addition; and 4) cooling profile after end of second water addition. An eight-trial, four-factor, orthogonal array experimental design was used to screen these parameters, and it was found that only two of those four actually had a significant effect on interconversion to the more thermodynamically stable polymorph A: 2) rate of second water addition and 4) cooling profile.

Figure 11:
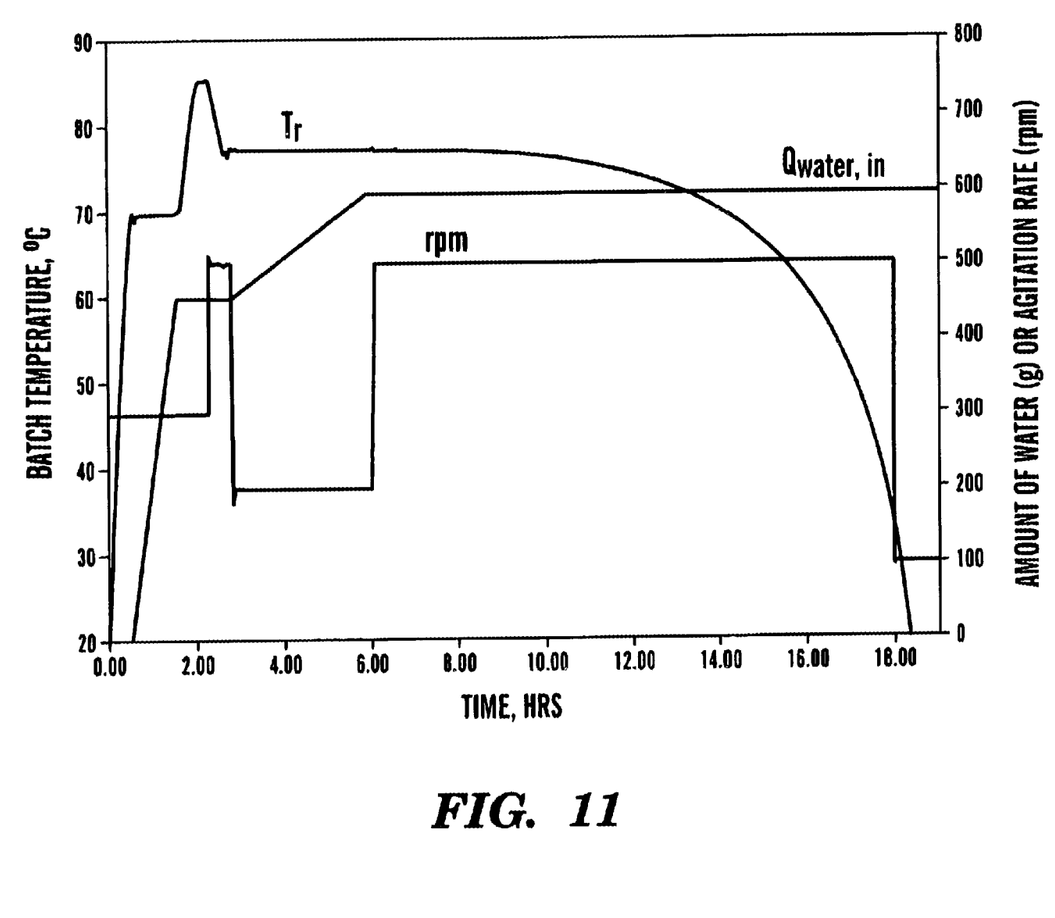
FIG. 11 is a graphic representation of the time-course of three parameters (temperature, volume of water added and stirring rate) in a process of the invention.

The cooling curve, the addition profile of the anti-solvent (water) and the stirring rate, are shown in FIG. 11. The effect of the cooling curve on the polymorph obtained was examined. As the cooling type was changed from a 4-hour linear cooling profile to a non-linear 12 hour cooling profile, the mean polymorph form value dropped from 39% form B to a value of <5% form B. The effect of anti-solvent addition time on polymorph ratio was also examined. As the addition time was increased from 15 minutes to 3 hours, the mean level of polymorph B dropped from 37% to <5%. Significant interaction between cooling profile and addition time was observed, as illustrated in Table 8. The effect of addition time on polymorph form is different as the cooling profile is changed from a 4-hour linear to a 12-hour non-linear cooling. A single non-linear 12-hour profile produces the desired polymorph A with minimal contribution from addition time.

TABLE 8

Interaction of Cooling Type and Addition Time

| Cooling Type | Addition Time, min | Mean Value of form B, % |
|---|---|---|
| 4-hr Linear | 15 | 70.0% |
| 4-hr Linear | 180 | 7.7% |
| 12-hr Non-Linear | 15 | 4.65% |
| 12-hr Non-Linear | 180 | 2.23% |

Figure 12:
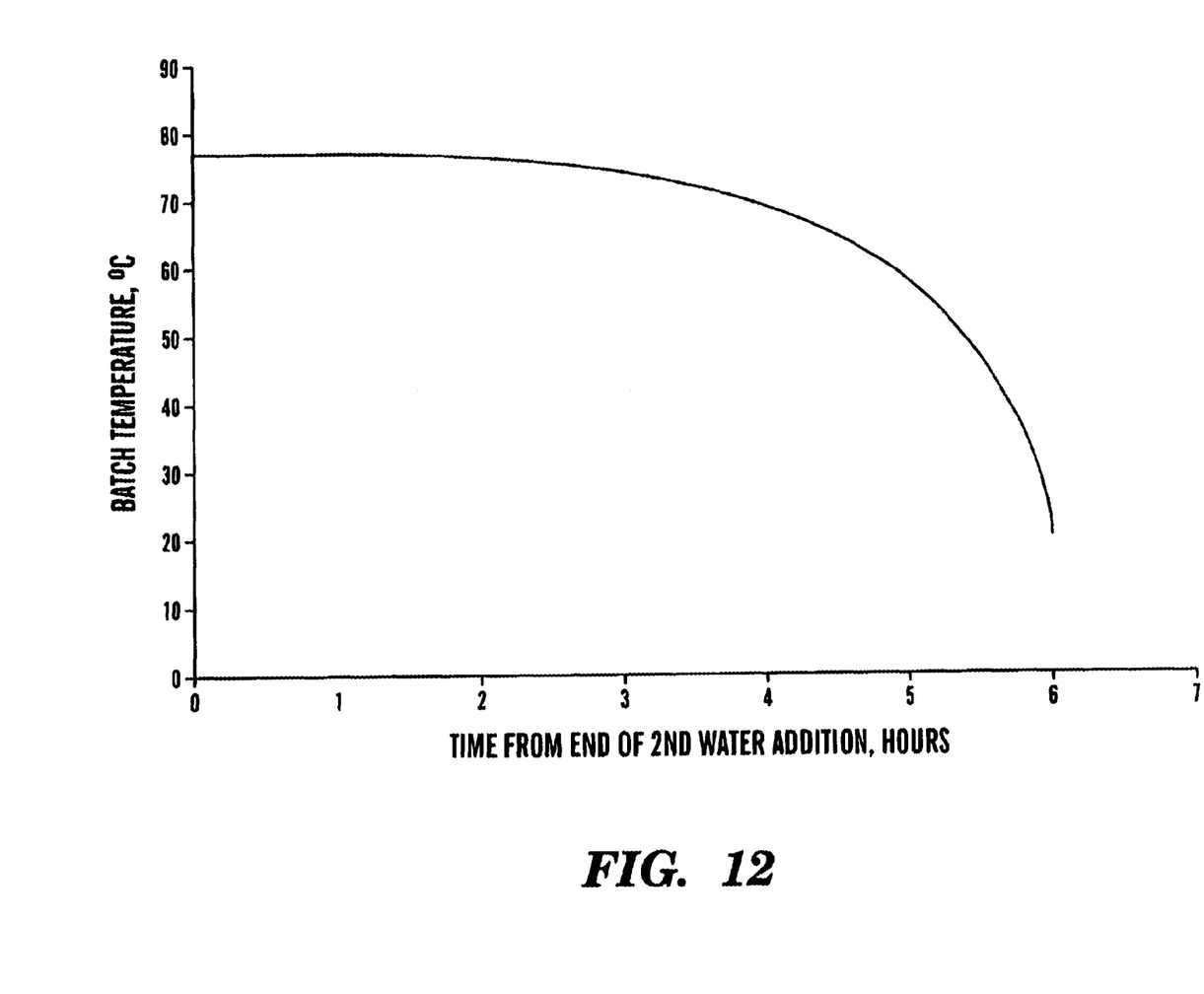
FIG. 12 is a graphic representation of the temperature time during the claimed process.

FIG. 12 illustrates the crystallization cooling profile adopted for controlling the polymorph selectivity following a 2-hour water addition. The ideal cooling curve is approximately described by a third order polynomial equation:

$$T = -0.7788 \cdot t^3 + 4.623 \cdot t^2 - 8.7012 \cdot t + 80.87$$

wherein T represents batch temperature in degrees centigrade and t represents time in hours.

This is an adequate description of the curve to produce highly satisfactory results, although it can be further refined by adjustment for the expected variability of solute initial concentration and for temperature measurement errors. This cooling regime allows control of constant small supersaturation during cooling to ensure that the thermodynamically stable polymorph A exclusively grows. Any significant increase in supersaturation, due to either natural cooling or linear cooling, generates a significant amount of the metastable polymorph B that may not have a chance to interconvert back to A before isolation. Control of constant supersaturation through slow cooling is important at the higher temperatures during the early stages of cooling because that is where the solubility difference between the two polymorphs is the highest and that is also where most of the product comes out of solution. Experiments were carried out on 2 liter, 50 liter and 1200 liter scales using the above cooling profile. All resulted in >95% of polymorph A. The time and temperature coordinates of the typical profile (FIG. 12) are shown in Table 9.

TABLE 9

| Time, hrs. | Temperature ° C. |
|---|---|
| 0.00 | 77.3 |
| 0.17 | 77.3 |
| 0.33 | 77.3 |
| 0.50 | 77.3 |
| 0.67 | 77.2 |
| 0.83 | 77.2 |
| 1.00 | 77.2 |
| 1.17 | 77.1 |
| 1.33 | 77.0 |
| 1.50 | 76.9 |
| 1.67 | 76.7 |
| 1.83 | 76.6 |
| 2.00 | 76.4 |
| 2.17 | 76.1 |
| 2.33 | 75.8 |
| 2.50 | 75.5 |
| 2.67 | 75.1 |
| 2.83 | 74.7 |
| 3.00 | 74.1 |
| 3.17 | 73.6 |
| 3.33 | 72.9 |
| 3.50 | 72.1 |
| 3.67 | 71.2 |
| 3.83 | 70.2 |
| 4.00 | 69.1 |
| 4.17 | 67.8 |
| 4.33 | 66.3 |
| 4.50 | 64.6 |
| 4.67 | 62.6 |
| 4.83 | 60.3 |
| 5.00 | 57.7 |
| 5.17 | 54.5 |
| 5.33 | 50.7 |
| 5.50 | 46.1 |
| 5.67 | 40.2 |
| 5.83 | 32.2 |
| 6.00 | 20.0 |
| 6.00 | 20.0 |
| 6.00 | 20.0 |
| 6.00 | 20.0 |
| 6.00 | 20.0 |

In the foregoing experiments, mixing energy proved not to be a critical factor for polymorph control, but it was important for particle size distribution control. The present invention relates to polymorphs of norastemizole, rather than particle size, but particle size is often another important variable in determining bioavailability and formulation of solid dosage forms. The effects of agitation rate, cooling profile and hold time on particle size distribution appear to be interdependent. During crystallization, for instance, increased agitation/energy dissipation increases particle size through improved mass transfer and growth rate, while, at the same time, reduces particle size during the cooling/aging profile through a secondary nucleation-particle break-up mechanism. Agitation has a different effect on different regions of the crystallization. Most of the significant effect is during the final cool-down period, during which polymorph A predominates. This suggests a high agitation rate during initial stages of crystallization until interconversion to form A is completed. During the final cooling down stage, lowering the agitation favors a larger particle size distribution. We have found that, as the agitation rate increases, (initial agitation dominates PSD) the mean size also increases from 41.2 to 76.5 microns. Additionally, as the hold time following the water addition (high temperature region) is extended from 15 minutes to 225 minutes, the mean particle size increases from 65.6 microns to 113.9 microns (favors fewer primary nuclei and more crystal growth). Significant interaction between the two factors is also observed, with maximum mean size obtained (151.2 microns) at the low agitation level and 225 minute post addition hold time, while the smallest mean particle size is observed during the low agitation level and short post addition hold time (60.6 microns).

Applicants have found that the critical process parameters are interdependent, and without controlling both the cooling curve and the rate of anti-solvent addition, either form B or a mixture of polymorphic forms will be produced. All prior processes for producing norastemizole free base, described in art known to the applicants, were examined. The results are summarized below. The samples were generated following the referenced procedures and were tested using the validated XRPD method. Table 10 summarizes the results, which clearly show that the procedures described in all the references produce predominantly or exclusively the undesirable, kinetically favored polymorph B.

TABLE 10

Comparison of Processes in Literature

| Sample Label | Polymorph Results, % Form B | Reference Sample Source |
|---|---|---|
| H1632-4A | 91% | Janssen et al. U.S. Pat. No. 4,695,569, column 24, lines 22–32 |
| H1632-5A | 90% | Maynard et al. U.S. Pat. No. 5,922,737, column 39, lines 20–30 |
| H1632-6A | 100% | Hong et al. U.S. Pat. No. 5,817,823 column 32, lines 9–18 |
| R1632-7A | 86% | Hong et al. U.S. Pat. No. 5,817,823 column 33, lines 16–23 |
| H1632-8A | Most likely all Form B[1] | Hong et al. U.S. Pat. No. 5,817,823 column 43, lines 19–24 |
| H1632-30A | 100% | Hong et al. U.S. Pat. No. 5,817,823 column 36, lines 31–41 Note: concentration conducted using a rotary evaporator to half filtration volume before dilution with water (370 ml). |

[1]Sample had the same XRPD pattern as sample H1632-6A but could not be sufficiently fit using Rietveld analysis due to intense reflections at approximately 26 and 30 °2θ. The sample does not contain polymorph A The procedure for reducing the volume is not disclosed in Hong et al. U.S. Pat. No. 5,817,823 column 36, lines 31–34, but the person of ordinary skill would normally reduce volume on a rotary evaporator under vacuum, (the procedure used in the table). As a check on applicants discovery of the result-effective variables, a parallel experiment to the one identified as H1632-30A was run. In the parallel experiment, concentration was carried out by atmospheric pressure distillation for an extended period to reduce the solution to half-filtration volume before dilution with water. As would be predicted from the results of applicants studies described above, this provided predominantly the A polymorph.

The process for producing crystalline norastemizole of greater than 95% polymorph A comprises:

(a) dissolving norasternizole in a solvent at a temperature between 70° C. and 110° C., (b) adding an amount of anti-solvent sufficient to initiate crystallization at a temperature above 70° C.;

(c) stirring at a temperature above 70° C. for at least one hour;

(d) adding a second portion of anti-solvent at a temperature above 70° C. and over a period of at least 2 hours, said second portion of anti-solvent being of sufficient amount to produce ultimate crystallization of at least 85% of said norastemizole; and (e) stirring and cooling from above 70° C. to below 30° C. over the course of at least 6 hours in a non-linear fashion such that no more than a 15% temperature drop occurs in the first 3 hours.

Possible solvents include lower alkanols, THF, acetone and glycol ethers. DMF and DMSO are also possible, but their high boiling points make them unattractive for a number of reasons. Water is the preferred anti-solvent, although one could consider alkanes. Preferably the norastemizole is dissolved in ethanol at about 78° C. (the boiling point) and an amount of water just sufficient to initiate crystallization is added at or near reflux. The mixture is stirred at a temperature above 70° C. for at least one hour; and a second portion of water is added at a temperature above 70° C. and over a period of at least 2 hours. The mixture is stirred and cooled from above 70° C. to room temperature over the course of at least 6 hours in a non-linear fashion, such that the temperature remains above 70° C. for the first three hours. More preferably, the norastemizole is dissolved in about 4 parts by weight of ethanol at reflux; 6 to 7 parts by weight of water is added and the mix is stirred at a temperature above 70° C. for at least one hour. (Parts by weight are relative to norastemizole.) A second portion of about 2 parts by weight of water is added over a period of at least 2 hours at a temperature above 70° C., and the mixture is stirred and cooled from above 70° C. to room temperature over the course of at least 6 hours in a non-linear fashion as shown in FIG. 12. Most preferably, the norastemizole is dissolved in 3.9 parts by weight of ethanol at reflux; 6.5 parts by weight of water is added and the mix is stirred at a temperature above 70° C. for at least one hour. A second portion of 2 parts by weight of water is added over a period of at least 2 hours at a temperature above 70° C., and the mixture is stirred and cooled from above 70° C. to room temperature over the course of at least 6 hours in a non-linear fashion as shown in FIG. 12. When a supply of seeds of polymorph A is available, the process is improved by seeding after the first addition of anti-solvent.

The pharmaceutical compositions of the present invention comprise polymorph A of norastemizole as the active ingredient, together with one or more pharmaceutically acceptable carriers for solid dosage forms. Tablets and capsules may be prepared by methods well known in the pharmaceutical art. (See Remington: The Science and Practice of Pharmacy 19th Edition 1995, Chapter 94). U.S. Pat. No. 6,124,320 discloses methods of treating mammals with norastemizole and compositions therfor. The disclosures of both are incorporated herein by reference.

What is claimed is:

1. Norastemizole in the form of a crystalline solid comprising at least 95% of a first polymorph having peaks at the diffraction degrees with the intensity shown below in an X-ray powder diffraction pattern:

| No. | 2θ | d |
|---|---|---|
| 1 | 9.0329 | 6.78217 |
| 2 | 10.24 | 8.63159 |
| 3 | 10.588 | 8.34866 |
| 4 | 11.7273 | 7.54003 |
| 5 | 12.5417 | 7.05218 |
| 6 | 13.38 | 6.61217 |
| 7 | 13.6284 | 6.4922 |
| 8 | 14.5846 | 6.06864 |
| 9 | 15.8358 | 5.59185 |
| 10 | 17.26 | 5.13352 |
| 11 | 18.1 | 4.89713 |
| 12 | 19.32 | 4.59055 |
| 13 | 19.62 | 4.52103 |
| 14 | 20.12 | 4.40979 |
| 15 | 20.5005 | 4.3288 |
| 16 | 20.9946 | 4.22802 |
| 17 | 21.22 | 4.18362 |
| 18 | 21.8351 | 4.06714 |
| 19 | 22.0887 | 4.02101 |
| 20 | 22.9427 | 3.87323 |
| 21 | 23.56 | 3.77313 |
| 22 | 24.7 | 3.6015 |
| 23 | 25.4419 | 3.49814 |
| 24 | 26.98 | 3.3021 |
| 25 | 27.5 | 3.24083 |
| 26 | 27.98 | 3.18632 |
| 27 | 29 | 3.07652 |
| 28 | 29.46 | 3.02952 |
| 29 | 29.8 | 2.99573 |
| 30 | 30.66 | 2.91363 |
| 31 | 31.0238 | 2.88029 |
| 32 | 31.991 | 2.79538 |
| 33 | 32.8 | 2.72826. |

2. A process for producing crystalline norastemizole as defined in claim 1 comprising:

(a) dissolving norastemizole in a solvent, said solvent being in an amount sufficient to achieve dissolution of said norastemizole at a first temperature;

(b) adding an amount of anti-solvent just sufficient to initiate crystallization at said first temperature, whereby less than 5% of said norastemizole crystallizes;

(c) stirring at said first temperature for a first period of time to allow crystallization of less than 5% of said norastemizole and equilibration of said norastemizole to greater than 95% of the polymorph of claim 1;

(d) adding a second portion of anti-solvent at said first temperature and over a second period of time such that norastemizole that crystallizes during said adding said second portion of anti-solvent is greater than 95% of the polymorph of claim 1, said second portion of anti-solvent being of sufficient amount to produce ultimate crystallization of at least 85% of said norastemizole at a second temperature, said second temperature being lower than said first temperature; and (e) stirring and cooling from said first temperature to said second temperature in a non-linear fashion over a third period of time such that no more than a 15% temperature drop occurs in the first half of said third period of time, whereby at least 85% of said norasternizole is crystallized and greater than 95% of said norastemizole is in the form of the polymorph of claim 1.

3. A process for producing crystalline norastemizole as defined in claim 1 comprising:

(a) dissolving norastemizole in a solvent at a temperature between 70° C. and 110° C.;

(b) adding an amount of anti-solvent sufficient to initiate crystallization at a temperature above 70° C.;

(c) stirring at a temperature above 70° C. for at least one hour;

(d) adding a second portion of anti-solvent at a temperature above 70° C. and over a period of at least 2 hours, said second portion of anti-solvent being of sufficient amount to produce ultimate crystallization of at least 85% of said norastemizole; and (e) stirring and cooling from above 70° C. to below 30° C. over the course of at least 6 hours in a non-linear fashion such that no more than a 15% temperature drop occurs in the first 3 hours.

4. A process for producing crystalline norastemizole comprising:

(a) dissolving norastemizole in ethanol at about 78° C.;

(b) adding an amount of water sufficient to initiate crystallization at reflux;

(c) stirring at a temperature above 70° C. for at least one hour;

(d) adding a second portion of water at a temperature above 70° C. and over a period of at least 2 hours;

(e) stirring and cooling from above 70° C. to room temperature over the course of at least 6 hours in a non-linear fashion such that the temperature remains above 70° C. for the first three hours.

5. A process for producing crystalline norastemizole comprising:

(a) dissolving norasternizole in about 4 parts by weight of ethanol at reflux;

(b) adding from 6 to 7 parts by weight of water;

(c) stirring at a temperature above 70° C. for at least one hour;

(d) adding a second portion of about 2 parts by weight of water at a temperature above 70° C. and over a period of at least 2 hours;

(e) stirring and cooling from above 70° C. to room temperature over the course of at least 6 hours in a non-linear fashion, such that the temperature remains between 78° C. and 70° C. for the first three hours.

6. A process for producing crystalline norastemizole comprising:

(a) dissolving norastemizole in about 4 parts by weight of ethanol at reflux;

(b) adding about 6.5 parts by weight of water;

(c) seeding with crystals comprising greater than 95% by weight of a polymorph of norastemizole having peaks at the diffraction degrees with the intensity shown below in an X-ray powder diffraction pattern:

| No. | 2θ | d |
|---|---|---|
| 1 | 9.0329 | 6.78217 |
| 2 | 10.24 | 8.63159 |

-continued

| No. | 2θ | d |
|---|---|---|
| 3 | 10.588 | 8.34866 |
| 4 | 11.7273 | 7.54003 |
| 5 | 12.5417 | 7.05218 |
| 6 | 13.38 | 6.61217 |
| 7 | 13.6284 | 6.4922 |
| 8 | 14.5846 | 6.06864 |
| 9 | 15.8358 | 5.59185 |
| 10 | 17.26 | 5.13352 |
| 11 | 18.1 | 4.89713 |
| 12 | 19.32 | 4.59055 |
| 13 | 19.62 | 4.52103 |
| 14 | 20.12 | 4.40979 |
| 15 | 20.5005 | 4.3288 |
| 16 | 20.9946 | 4.22802 |
| 17 | 21.22 | 4.18362 |
| 18 | 21.8351 | 4.06714 |
| 19 | 22.0887 | 4.02101 |
| 20 | 22.9427 | 3.87323 |
| 21 | 23.56 | 3.77313 |
| 22 | 24.7 | 3.6015 |
| 23 | 25.4419 | 3.49814 |
| 24 | 26.98 | 3.3021 |
| 25 | 27.5 | 3.24083 |
| 26 | 27.98 | 3.18632 |
| 27 | 29 | 3.07652 |
| 28 | 29.46 | 3.02952 |
| 29 | 29.8 | 2.99573 |
| 30 | 30.66 | 2.91363 |
| 31 | 31.0238 | 2.88029 |
| 32 | 31.991 | 2.79538 |
| 33 | 32.8 | 2.72826 |

(d) stirring at a temperature above 70° C. for at least one hour;

(e) adding a second portion of about 2 parts by weight of water at a temperature above 70° C. and over a period of at least 2 hours;

(f) stirring and cooling from above 70° C. to room temperature over the course of at least 6 hours in a non-linear fashion, such that the temperature remains between 78° C. and 70° C. for the first three hours.

7. Crystalline norastemizole produced by the process of claim 2.

8. Crystalline norastemizole produced by the process of claim 3.

9. Crystalline norastemizole produced by the process of claim 4.

10. Crystalline norastemizole produced by the process of claim 5.

11. Crystalline norastemizole produced by the process of claim 6.

12. A method for treating allergic conditions in a mammal comprising administering to said mammal a therapeutically effective amount of the solid norastemizole of claim 1.

13. A pharmaceutical composition comprising a pharmaceutically acceptable carrier for a solid dosage form and the solid norastemizole of claim 1.

* * * * *